United States Patent [19]

Souvie

[11] Patent Number: 5,142,053

[45] Date of Patent: Aug. 25, 1992

[54] PROCESS FOR THE PREPARATION OF 1-(2,3,4-TRIMETHOXYBENZYL)PIPERAZINE BY REDUCTIVE ANIMATION

[75] Inventor: Jean-Claude Souvie, Bolbec, France

[73] Assignee: Adir et Compagnie, Courbevoie, France

[21] Appl. No.: 688,736

[22] Filed: Apr. 19, 1991

[30] Foreign Application Priority Data

Apr. 20, 1990 [FR] France ............... 90 05027

[51] Int. Cl.$^5$ .......................... C07D 295/73
[52] U.S. Cl. ..................................... 544/398
[58] Field of Search ........................ 544/398

[56] References Cited

U.S. PATENT DOCUMENTS 3,951,970  4/1976  Razdan et al. ............. 544/398
3,996,278  12/1976  Schlager ..................... 544/398

FOREIGN PATENT DOCUMENTS 97884    2/1964  Denmark ................. 544/398
BSM805M  9/1961  France .
1302958  1/1962  France .
2493316  11/1980  France .
59766    5/1981  Japan ...................... 544/398

OTHER PUBLICATIONS

Chemical Abstracts, vol. 79, 1973, p. 462 #32098k (abstracting Kokai 73 32,889; JP 48032889).

Primary Examiner—Cecilia Shen
Attorney, Agent, or Firm—Gordon W. Hueschen

[57] ABSTRACT

The invention relates to a process for the preparation of the compound of formula I:

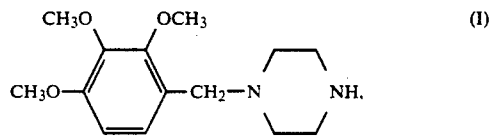

characterized in that 2,3,4-trimethoxybenzaldehyde is dissolved with piperazine, and then the reaction medium is subjected to the action of hydrogen to give the compound of formula I.

8 Claims, No Drawings

PROCESS FOR THE PREPARATION OF 1-(2,3,4-TRIMETHOXYBENZYL)PIPERAZINE BY REDUCTIVE ANIMATION

The present invention relates to a new industrial process for the preparation of 1-(2,3,4-trimethoxybenzyl)-piperazine.

This compound, which is also known by the INN trimetazidine, has very valuable pharmacological properties. In particular, it has vasodilatory properties; it safeguards energy metabolism of the cell exposed to hypoxia or ischaemia and prevents the collapse of the intracellular level of ATP.

Several methods of preparing that compound are already known. However, none of the processes already described in the literature enables trimetazidine to be obtained with satisfactory purity and in good yield.

The process for preparing 1-(2,3,4-trimethoxybenzyl)piperazine advocated in BSM (Special Medicament Patent) No. 805 M consists in obtaining that compound by condensing 2,3,4-trimethoxybenzyl chloride with 1-formylpiperazine. The condensation product is then hydrolysed to give 1-(2,3,4-trimethoxybenzyl)piperazine, which is treated with gaseous hydrochloric acid to give the corresponding dihydrochloride.

This process gives a crude material of average purity in a yield that is not very satisfactory. Several purifications are therefore necessary to give a "pharmaceutical grade" product.

Furthermore, French Patent No. 1.302958 describes various processes for the preparation of trialkoxylated 1-benzylpiperazine compounds, and in particular of 1-(2,3,4-trimethoxybenzyl)piperazine.

However, all these processes generally require several steps and enable trimetazidine to be obtained only in yields that do not exceed 43%.

The processes described also lead to the formation of a large number of by-products.

Another process for the preparation of trimetazidine is described in French Patent No. 2493316. This process consists in reacting, in a first solvent, 2,3,4-trimethoxy-benzyl chloride with piperazin-2-one to give 4-(2,3,4-trimethoxybenzyl)piperazin-2-one and then, in a second phase, reducing that compound in a second solvent, by means of a hydride, to give the desired compound. This process necessarily entails the preparation of piperazin-2-one, which is not a commercial product.

Patent JP 48032889 describes a process for the preparation of trimetazidine from 2,3,4-trimethoxybenzaldehyde and hexahydrated piperazine. The reaction is carried out at from 80° to 90° C. in the presence of formic acid for from 10 to 18 hours, and the yield is in the region of 38%.

In view of the therapeutic value of trimetazidine and the absence of a process by means of which it can be obtained in good yield, with satisfactory purity and, if possible, from inexpensive, commercially available starting materials, more detailed research was undertaken and has led to the discovery of a new process for the preparation of 1-(2,3,4-trimethoxybenzyl)piperazine and the corresponding dihydrochloride.

By means of this process it is possible to obtain the trimetazidine base in one step starting from commercial compounds, in a yield greater than 90% and with very satisfactory purity.

The invention relates more precisely to a process for the preparation of 1-(2,3,4-trimethoxybenzyl)piperazine, the compound of formula I:

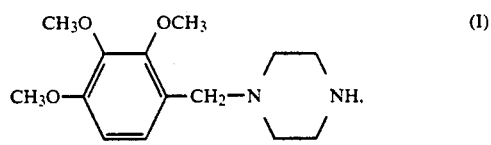

characterised in that 2,3,4-trimethoxybenzaldehyde, the compound of formula II:

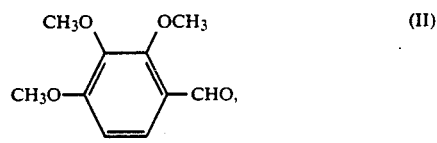

is dissolved with piperazine, the compound of formula III:

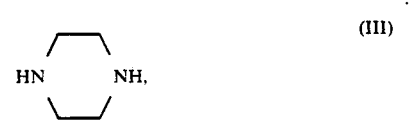

in an alcoholic solvent or in methyl tert.-butyl ether (MTBE), the solution so obtained is then subjected to the action of hydrogen, in the presence of a hydrogenation catalyst, at a temperature of from 45° to 75° C., to give the compound of formula I, there are then separated from the reaction medium first the excess piperazine, and then the compound of formula I in base form, which compound, if desired, is then converted into its addition salts with a pharmaceutically acceptable organic or mineral acid.

The starting materials, 2,3,4-trimethoxybenzaldehyde and piperazine, are commercial products.

(2,3,4-trimethoxybenzaldehyde supplied by FINOR-GA® and anhydrous piperazine supplied by BASF®.)

In the reaction, the compounds of formulae II and III are dissolved either in a low molecular weight alcohol, such as ethanol or isopropanol, or, preferably, in MTBE.

5% Pd/C or 5% Pt/C may be used as hydrogenation catalyst. The use of 5% Pd/C is preferred.

An excess of piperazine is required in the reaction, and the molar ratio of 2,3,4-trimethoxybenzaldehyde to piperazine must, in fact, be 1:2–1:4.

In the hydrogenation, the temperature at the start may be set at from 45° to 55° C. It then stabilises during hydrogenation at approximately from 70° to 75° C. The hydrogen pressure is preferably set at from 5 to 10 bar.

When MTBE is used as the solvent, the excess piperazine is isolated at the end of the reaction, after cooling the reaction medium, by simple precipitation.

The piperazine so isolated, in the pure state, may be used later. As regards the trimetazidine, it is isolated from the reaction medium by double extraction.

Thus, after the piperazine has been removed and the pH of the reaction medium has been adjusted to from 7.5 to 8.3, the trimetazidine is extracted with water and then, after alkalisation, with toluene.

The following Examples, which are not limiting, illustrate the invention.

EXAMPLE 1

Preparation of Trimetazidine by Reductive Amination Using MTBE as Reaction Solvent 78.4 g of 2,3,4-trimethoxybenzaldehyde, 68.8 g of piperazine, 400 ml of MTBE and 4 g of 5% Pd/C (Engelhard ®) are introduced into a reactor.

Purging is carried out with nitrogen and hydrogen, and then the whole is heated as quickly as possible.

When the temperature has reached approximately from 50° to 55° C., hydrogenation is carried out under 10 bar and heating is continued to 70° C.

The hydrogenation is stopped after approximately 2 hours. The whole is cooled to 50° C. and filtered to remove the catalyst.

The filtrate is recovered and cooled to approximately 10° C. in order to remove the unreacted piperazine by precipitation. The whole is then filtered.

200 ml of water are added to the filtrate at from 13° to 18° C., and the pH is adjusted to from 7.9 to 8.0 by the addition of 7N hydrochloric acid.

The solution is then diluted to half its concentration with water.

The organic phase is removed and the aqueous phase is extracted twice with 100 ml of toluene. The toluene is then removed.

The aqueous phase is then rendered alkaline, with cooling in an ice-bath, by the addition of 42 g of sodium hydroxide in the form of pellets.

The trimetazidine base thus precipitated is extracted 3 times with 120 ml of toluene. The toluene extracts are dried on anhydrous magnesium sulphate and evaporated to dryness.

Yield: 94%.
Purity of the trimetazidine (HPLC): 99.5%.

EXAMPLE 2

Preparation of Trimetazidine By Reductive Amination Using Ethanol as Reaction Solvent 78.4 g of 2,3,4-trimethoxybenzaldehyde, 137.6 g of anhydrous piperazine, 400 ml of ethanol and 4 g of 5% Pd/C are introduced into a reactor.

Purging is carried out with nitrogen and hydrogen, and then the whole is heated as quickly as possible to 70° C. When the temperature has reached 50° C., hydrogenation is carried out under 10 bar. The hydrogenation is stopped after 70 minutes.

The reaction medium is filtered at 20° C. and the clear yellow filtrate is recovered and evaporated to dryness.

The pasty residue is taken up in 200 ml of iced toluene at from −5° to −10° C.

The precipitated piperazine is removed by filtration.

200 ml of water are added to the toluene filtrate and the pH is adjusted to 6 by the addition of concentrated hydrochloric acid. Decantation is carried out followed by extraction twice more with 120 ml of toluene.

The organic phases are removed and then the mixture is rendered alkaline with 42 g of sodium hydroxide in the form of flakes. The trimetazidine precipitates.

Extraction is carried out three times with 120 ml of toluene. The toluene phases are combined and then evaporated to dryness in order to isolate the trimetazidine base.

Yield: 92%.
Purity of the trimetazidine (HPLC): 96.8%.

EXAMPLE 3

Preparation of Trimetazidine Dihydrochloride 216.0 g of isopropanol and 100.1 g of trimetazidine base obtained in Example 1 are introduced, with stirring, into a reactor under a nitrogen atmosphere.

The whole is stirred until the base has dissolved completely.

The mixture is filtered and the clear solution of trimetazidine base is collected in a stainless steel container. The reactor is rinsed with 15.7 g of isopropanol, and the isopropanol used for rinsing is mixed with the trimetazidine solution.

348 g of isopropanol and 79.2 g of concentrated hydrochloric acid (36%) are introduced into a reactor under a nitrogen atmosphere.

The solution of trimetazidine base is then poured onto that solution with stirring, without exceeding 40° C.

The medium is then concentrated under normal pressure until an evaporate weight of 270 g is obtained.

The suspension so obtained is cooled to 0° C. and maintained at that temperature for one hour with stirring and under a nitrogen atmosphere.

The suspension is then filtered in order to isolate the trimetazidine dihydrochloride, which salt is then washed twice with isopropanol.

Yield: 99%.
Purity of the trimetazidine dihydrochloride (HPLC): 100%.

I claim:

1. Process for the preparation of 1-(2,3,4-trimethoxybenzyl)piperazine, the compound of formula I:

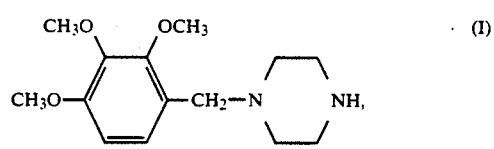

characterised in that 2,3,4-trimethoxybenzaldehyde, the compound of formula II:

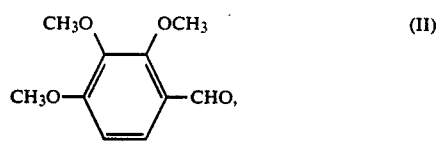

is dissolved together with an excess of piperazine, the compound of formula III:

in an alcoholic solvent or in methyl tert.-butyl ether, the solution so obtained is then subjected to the action of hydrogen, in the presence of a hydrogenation catalyst, to give the compound of formula I, there are then separated from the reaction medium first the excess piperazine, and then the compound of formula I in base form, which compound, if desired, is then converted into an addition salt with a pharmaceutically-acceptable organic or mineral acid.

2. Process according to claim 1, characterised in that the compounds of formulae II and III are dissolved in methyl tert.-butyl ether.

3. Process according to claim 1, characterised in that the hydrogenation is carried out at a temperature of 45° to 75° C.

4. Process according to claim 3, characterised in that the hydrogenation is carried out at a temperature of 50° to 70° C.

5. Process according to claim 1, characterised in that 5% palladium-on-carbon is used as hydrogenation catalyst.

6. Process according to claim 1, characterised in that the molar ratio of 2,3,4-trimethoxybenzaldehyde to piperazine is 1:2.

7. Process according to claim 1, characterised in that the compounds of formulae II and III are dissolved in methyl tert.-butyl ether and in that the excess piperazine, after the reaction, is removed from the reaction medium by precipitation.

8. Process according to claim 1, characterized in that the molar ratio of 2,3,4-trimethoxybenzaldehyde to piperazine is between about 1:2 and 1:4.

* * * * *

UNITED STATES PATENT AND TRADEMARK OFFICE
CERTIFICATE OF CORRECTION

PATENT NO. :  5,142,053
DATED     :  Aug. 25, 1992
INVENTOR(S) :  Jean-Claude Souvie It is certified that error appears in the above-identified patent and that said Letters Patent is hereby corrected as shown below:

```
Title Page, Column 1, [54], last line; "ANIMATION" should read
    -- AMINATION --.  (Amdt. 2-3-92)
Column 1, line 4; "ANIMATION" should read --AMINATION--.
    (Amendment 2-3-92)
Column 2, line 36; "there" should read -- they --.
Column 4, line 66; "there" should read -- they --.
```

Signed and Sealed this

Nineteenth Day of October, 1993

Attest:

BRUCE LEHMAN

*Attesting Officer*   *Commissioner of Patents and Trademarks*